US008603295B2

(12) United States Patent
Dottori et al.

(10) Patent No.: US 8,603,295 B2
(45) Date of Patent: Dec. 10, 2013

(54) SEPARATION OF REACTIVE CELLULOSE FROM LIGNOCELLULOSIC BIOMASS WITH HIGH LIGNIN CONTENT

(75) Inventors: Frank A. Dottori, Temiscaming (CA); Robert Ashley Cooper Benson, North Bay (CA); Régis-Olivier Benech, Chatham (CA)

(73) Assignee: Greenfield Specialty Alcohols Inc., Toronto, Ontario (CA)

( * ) Notice: Subject to any disclaimer, the term of this patent is extended or adjusted under 35 U.S.C. 154(b) by 462 days.

(21) Appl. No.: 12/766,339

(22) Filed: Apr. 23, 2010

(65) Prior Publication Data
US 2010/0269990 A1  Oct. 28, 2010

Related U.S. Application Data

(60) Provisional application No. 61/172,048, filed on Apr. 23, 2009.

(51) Int. Cl.
*D21C 3/20* (2006.01)
*D21B 1/36* (2006.01)
*D21C 3/22* (2006.01)

(52) U.S. Cl.
CPC ... *D21C 3/20* (2013.01); *D21B 1/36* (2013.01); *D21C 3/222* (2013.01)
USPC .................................. 162/22; 162/9; 162/21

(58) Field of Classification Search
CPC ............. D21C 3/20; D21C 3/222; D21B 1/36
USPC ................................................. 162/9, 21, 22
See application file for complete search history.

(56) References Cited

U.S. PATENT DOCUMENTS

| 4,409,032 A | 10/1983 | Paszner |
| 4,470,851 A | 9/1984 | Paszner |
| 4,764,596 A | 8/1988 | Lora |
| 4,966,650 A | 10/1990 | De Long |

(Continued)

FOREIGN PATENT DOCUMENTS

| CA | 2368872 | 10/2000 |
| CA | 2477196 | 8/2003 |

(Continued)

OTHER PUBLICATIONS

Gullichsen editor, Chemical Pulping 6A/6B, 1999, Fapet Oy, p. A28-A29, A66, A577, and chapter 20.*

(Continued)

*Primary Examiner* — Anthony Calandra
(74) *Attorney, Agent, or Firm* — Borden Ladner Gervais LLP

(57) ABSTRACT

A process for separating the components of lignocellulosic biomass for the purpose of producing a pure reactive cellulose is disclosed. The process has two stages. In the first stage, the lignocellulosic biomass is pretreated with steam, with or without an acid catalyst, and then pressed, with or without the presence of an eluent, to remove hemicellulose and other impurities. In the second stage, the pretreated biomass is extracted with a solvent such as ethanol with or without acid catalysts in order to remove lignin and release a purified cellulose stream. The extracted cellulose is then rapidly decompressed to rupture the fibrous structure. The process provides a purified cellulose stream that is relatively easy to hydrolyze with enzymes and ferment to biofuels and other chemicals such as ethanol.

23 Claims, 1 Drawing Sheet

(56) References Cited

U.S. PATENT DOCUMENTS

| | | | |
|---|---|---|---|
| 5,730,837 A | 3/1998 | Black | |
| 7,368,037 B2* | 5/2008 | Vaders | 162/234 |
| 2002/0069987 A1 | 6/2002 | Pye | |
| 2003/0041982 A1* | 3/2003 | Prior | 162/24 |
| 2007/0034345 A1 | 2/2007 | Petrus | |
| 2007/0259412 A1 | 11/2007 | Belanger | |
| 2008/0032344 A1* | 2/2008 | Fallavollita | 435/72 |
| 2008/0196847 A1* | 8/2008 | Pieter van Heiningen et al. | 162/9 |

FOREIGN PATENT DOCUMENTS

| | | |
|---|---|---|
| CA | 2595484 | 2/2008 |
| CA | 2701194 | 10/2010 |
| CA | 2701407 | 10/2010 |
| DE | 19730486 | 1/1999 |
| WO | 93/15261 | 8/1993 |
| WO | 97/36040 | 10/1997 |
| WO | 2009/031164 | 3/2009 |
| WO | 2009/108773 | 9/2009 |
| WO | 2009116070 | 9/2009 |

OTHER PUBLICATIONS

Azzam, "Pretreatment of cane bagasse with alkaline hydrogen peroxide for enzymatic hydrolysis of cellulose and ethanol fermentation", Journal Environ. Sci. Health, 1989, vol. 24, pp. 421-433.

Katzen et al., "Use of cellulosic feedstocks for alcohol production, Use of Cellulosic Feedstocks for Alcohol Production", The Alcohols Textbook, Chapter 5, Nothingham University Press, 1959. pp. 37-46.

Araque et al., "Evaluation of organosolv pretreatment for the conversion of *Pinus radiata* D. Don to ethanol", Enzyme and Microbial Technology, vol. 43, Aug. 5, 2008, pp. 214-219.

Pan et al., "Bioconversion of hybrid poplar to ethanol and co-products using an organosolv fractionation process: optimization of process yields", Biotechnol. Bioeng, Aug. 5, 2006, published online Mar. 7, 2006, vol. 94, No. 5, pp.

Arato et al., "The Lignol Approach to Biorefining of Woody Biomass to Produce Ethanol and Chemicals", Applied Biochemistry and Biotechnology, vol. 121-124, Mar. 2005, pp. 871-882.

Muurinen, "Organosolv pulping-A review and distillation study related to peroxyacid pulping", University of Oulu, Finland, http://herkules.oulu.fi/isbn9514256611/isbn9514256611.pdf, ISBN 951-42-5661-1, presented Jun. 30, 2000, 314 pages.

Yang et al., "Pretreatment: the key to unlocking low-cost cellulosic ethanol", Biofuels, Bioproducts and Biorefinering, Jan. 2008, published online Dec. 17, 2007, vol. 2, pp. 26-40.

International Application No. PCT/CA2010/000581, International Search Report dated Jul. 8, 2010.

Itoh et al., "Bioorganosolve pretreatments for simultaneous saccharification and fermentation of beech wood by ethanolysis and white rot fungi", Journal of Biotechnology, vol. 103, Aug. 15, 2003, pp. 273-280.

Chow et al., "Energy resources and global development", Science, vol. 302, Nov. 28, 2003, pp. 1528-1531.

Wyman, Handbook on Bioethanol: Production and Utilization, Jul. 1996, Taylor and Francis, United States of America, pp. 10-12.

Chum et al., "Biomass and Renewable Fuels", Fuel Processing Technology, Jun. 2001, vol. 71, Elsevier Science B. V., United States of America, pp. 187-195.

Nabarlatz et al., "Autohydrolysis of agricultural by-products for the production of xylo-oligasaccharides", Carbohydrate Polymers , Oct. 2006, vol. 69, Elsevier Science B.V., United States of America, pp. 20-28.

Shapouri et al., "Estimating the net energy balance of corn ethanol; An Economic Research Service Report", USDA Report 721, Jul. 1995, 13 pages.

Shapouri et al., "The Energy Balance of corn ethanol: an update", USDA Report 814,Jul. 2002, 19 pages.

Wald et al., "The Energy challenge: A Renewed push for ethanol, without the corn", New York Times, Apr. 17, 2007, 5 pages.

Greer, "Commercializing cellulosic ethanol", Biocycle, vol. 49, Nov. 2008, No. 11, 4 pages.

Hill et al. "Environmental, economic, and energetic costs and benefits of biodiesel and ethanol biofuels", Proc. Natl. Acad. Sci. USA, Jul. 25, 2006, vol. 103, No. 30, pp. 11206-11210.

Farrell et al., "Ethanol can contribute to energy and environmental goals", Science, Jan. 27, 2006, vol. 311, 23 pages.

Somerville, "Biofuels", Current biology, 2007, vol. 17, No. 4, pp. 115-119.

Schuetzle et al., "Alcohol fuels from biomass-Assessment of production technologies", Western Governors' Association National Biomass and Regional Partnership Report, Jul. 2007, pp. 1-119, (125 pages).

Neely, "Factors affecting the pretreatment of biomass with gaseous ozone", Biotechnology and Bioengineering, vol. XXVI, Jan. 1984, pp. 59-65.

Vidal et al., "Improvement of in vitro digestibility of poplar sawdust", Biomass, 1988, vol. 16, pp. 1-17.

Delmer et al., "Cellulose biosynthesis", American Society of Plant Physiologist, The Plant Cell, vol. 7, Jul. 1995, pp. 987-1000.

Morohoshi, "Chemical characterization of wood and its components", In Wood and cellulosic chemistry; Hon, D.N.S, Shiraishi, N., Eds.; Marcel Dekker, Inc.: New York, USA, 1991, pp. 331-392.

de Vrije et al, "Pretreatment of *Miscanthus* for Hydrogen Production by Thermotoga Elfii", International Journal of Hydrogen Energy, Nov.-Dec. 2002, vol. 27, pp. 1381-1390.

Ha et al., "Fine Structure in cellulose microfibrils: NMR evidence from onion and quince", The Plant Journal, Aug. 27, 1998, published 1998, vol. 16, No. 2, pp. 183-190.

Palmqvist et al., "Fermentation of lignocellulosic hydrolysates. II: Inhibitors and mechanisms of inhibition", Bioresource Technology, Aug. 2000, vol. 74, pp. 25-33.

Galbe et al., "A review of the production of ethanol from softwood", Appl Microbiol Biotechnol, vol. 59, published online Jul. 17, 2002, pp. 618-628.

Torget et al., "Dilute sulfuric acid pretreatment of hardwood bark", Bioresource Technology, vol. 35, 1991, pp. 239-246.

Donghai et al., "Effects of different pretreatment modes on the enzymatic digestibility of corn leaf and corn stalk", Chinese Journal of Eng., vol. 14, No. 6, 2006, pp. 796-801.

Sun et al., "Hydrolysis of lignocellulosic materials for ethanol production: A review", Bioresource Technology, vol. 83, 2002, pp. 1-11.

McMillan et al., "Pretreatment of lignocellulosic biomass", Biprocessing Branch, Alternative Fuels Division, National Renewable Energy Laboratory, 1994, American Chemical Society, pp. 292-324.

Fan et al., "The nature of lignocellulosics and their pretreatments for enzymatic hydrolysis", Advances in Biochemical Engineering, 1982 vol. 23, pp. 158-187.

Mosier et al., "Features of promising technologies for pretreatment of lignocellulosic biomass", Bioresource Technology, vol. 96, available online Sep. 29, 2004, pp. 673-686.

Henley et al., "Enzymatic saccharification of cellulose in membrane reactors", Enzyme Microb. Tech., vol. 2, Jul. 1980, pp. 206-208.

Berlin et al., "Inhibition of cellulase, xylanase and beta-glucosidase activities by softwood lignin preparations", Journal of Biotechnology, vol. 125, Sep. 1, 2006, pp. 198-209.

Chandra et al. "Substrate pretreatment: The key to effective enzymatic hydrolysis of lignocellulosics? ", Adv. Biochem Engin/Biotechnol., published online May 26, 2007, vol. 108, pp. 67-93.

Kassim, "Enzymatic and chemical hydrolysis of certain cellulosic materials", Agricultural Wastes, vol. 17, 1986, pp. 229-233.

Xu et al., "Enzymatic hydrolysis of pretreated soybean straw", Biomass and Bioenergy, vol. 31, Feb. 2007, pp. 162-167.

Vaccarino et al., "Effect of SO2NaOH and Na2CO3 pretreatments on the degradability and cellulase digestibility of grape Marc", Biological Wastes, vol. 20, 1987, pp. 79-88.

Silverstein et al., "A comparison of chemical pretreatment methods for improving saccharification of cotton stalks", Bioresource Technology, available online Dec. 8, 2006, No. 98, pp. 3000-3011.

(56) References Cited

OTHER PUBLICATIONS

Zhao et al., "Comparative study on chemical pretreatment methods for improving enzymatic digestibility of crofton weed stem", Bioresource Technology, available online Aug. 20, 2007, vol. 99, pp. 3729-3736.

Gaspar et al., "Corn fiber as a raw material for hemicellulose and ethanol production", Process Biochemistry, 2007, vol. 42, pp. 1135-1139.

Saha et al., "Ethanol production from alkaline peroxide pretreated enzymatically saccharified wheat straw", Biotechnol. Prog., published online Jan. 19, 2006, vol. 22, pp. 449-453.

Saha et al., "Enzymatic saccharification and fermentation of alkaline peroxide pretreated rice hulls to ethanol", Enzyme and Microbial Technology, vol. 41, 2007, pp. 528-532.

Mishima et al., "Comparative study on chemical pretreatments to accelerate enzymatic hydrolysis of aquatic macrophyte biomass used in water purification processes.", Bioresource Technology, available online Nov. 23, 2005, vol. 97, pp. 2166-2172.

Sun et al., "Characteristics of degraded cellulose obtained from steam-exploded wheat straw", Carbohydrate Research, available online Dec. 2, 2004, vol. 340, pp. 97-106.

Chum et al., "Evaluation of pretreatments of biomass for enzymatic hydrolysis of cellulose", Solar Energy Research Institute: Golden, Colorado, Oct. 1985, pp. 1-67.

Taherzadeh et al., "Acid-based hydrolysis processes for ethanol from lignocellulosic materials: A review", Biosources, 2007, vol. 2, No. 3, pp. 472-499.

Ruiz et al., "Evaluation of steam explosion pre-treatment for enzymatic hydrolysis of sunflower stalks", Enzyme and Microbial Technology, vol. 42, Jan. 2008, pp. 160-166.

Ballesteros et al., "Ethanol from lignocellulosic materials by a simultaneous saccharification and fermentation process (SFS) with *Kluyveromyces marxianus* CECT 10875", Process Biochemistry, vol. 39, 2004, pp. 1843-1848.

Negro et al., "Hydrothermal pretreatment conditions to enhance ethanol production from poplar biomass", Applied Biochemistry and Biotechnology, vol. 105-108, Mar. 2003, pp. 87-100.

Kurabi et al., "Enzymatic hydrolysis of steam exploded and ethanol organosolv-pretreated Douglas-fir by novel and commercial fungal cellulases", Applied Biochemistry and Biotechnology, vol. 121-124, Mar. 2005, pp. 219-230.

Varga et al., "Optimization of steam pretreatment for corn stover to enhance enzymatic digestibility", Applied Biochemistry and Biotechnology, 2004, 42 pages.

Eklund et al., "The influence of SO2 and H2SO4 impregnation of willow prior to steam pretreatment", Bioresource Engineering, vol. 52, 1995, pp. 225-229.

Yang et al., "Effect of xylan and lignin removal by batch and flowthrough pretreatment on the enzymatic digestibility of corn stover cellulose", Biotechnol. Bioeng, Apr. 5, 2004, published online Feb. 13, 2004, vol. 86, pp. 88-95.

Alizadeh et al., "Pretreatment of switchgrass by ammonia fiber explosion (AFEX)", Applied Biochemistry and Biotechnology, vol. 121-124, Mar. 2005, pp. 1133-1141.

Chundawat et al., "Effect of particle size based separation of milled corn stover on AFEX pretreatment and enzymatic digestibility", Biotechnology and Bioengineering, vol. 96, No. 2, Feb. 1, 2007, pp. 219-231.

Eggeman et al., "Process and economic analysis of pretreatment technologies", Bioresource Technology, vol. 96, available online Mar. 10, 2005, pp. 2019-2025.

Taherzadeh et al., "Enzyme-based hydrolysis processes for ethanol from lignocellulosic materials: A review", BioResources, 2007, vol. 2, No. 4, pp. 707-738.

Vazquez et al, "Enhancing the potential of oligosaccharides from corncob autohydrolysis as prebiotic food ingredients", Industrial Crops and Products, 24, Mar. 2006, pp. 152-159.

Moura et al., "In vitro fermentation of xylooligosaccharides from corncobs autohydrolysis by *Bifidobacterium* and *Lactobacuillus* strains", LWT, 40, Aug. 2007, pp. 963-972.

PCT/CA2011/050689 International Search Report dated Dec. 19, 2011.

European Patent Application No. 10766552.3 Extended European Search Report dated Sep. 26, 2012.

\* cited by examiner

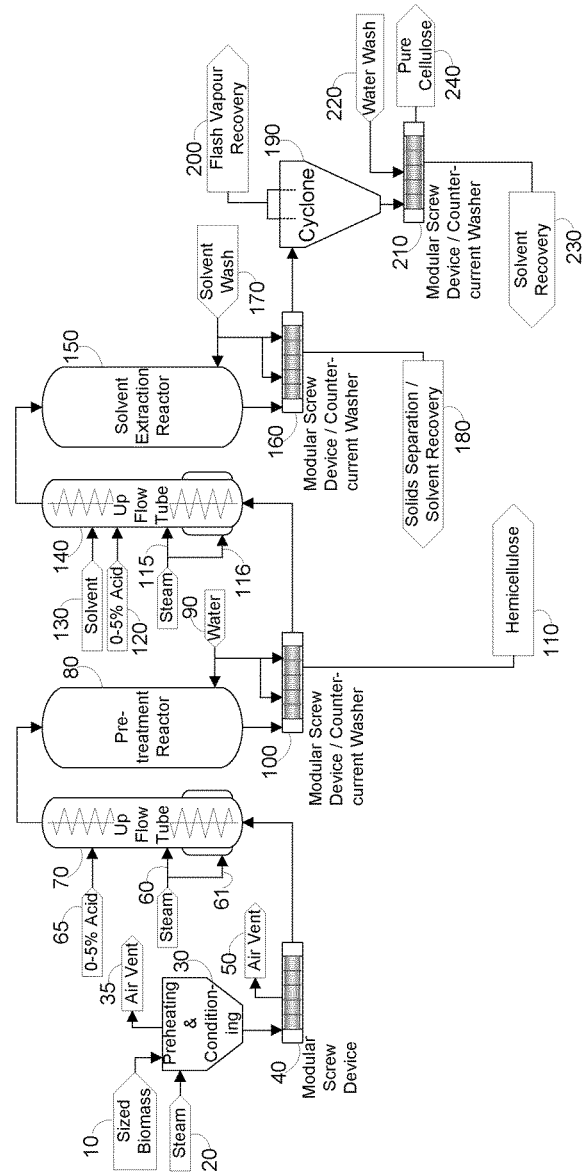

SEPARATION OF REACTIVE CELLULOSE FROM LIGNOCELLULOSIC BIOMASS WITH HIGH LIGNIN CONTENT

CROSS REFERENCE TO RELATED APPLICATIONS

This application claims the benefit of priority of U.S. Provisional Patent Application No. 61/172,048 filed Apr. 23, 2009, the contents of which is incorporated herein by reference.

FIELD OF THE INVENTION

The invention relates to a process for fractionating lignocellulosic biomass. In particular, the invention relates to a process for fractionating lignocellulosic biomass into three or more components, specifically cellulose, hemicellulose, lignin and other minor constituents of the biomass present in smaller amounts.

BACKGROUND AND DESCRIPTION OF PRIOR ART

There is a growing demand for transportation fuels made from renewable feedstocks. These renewable fuels displace fossil fuels resulting in a reduction of greenhouse gas emissions, along with other benefits.

In North America fuel ethanol is the major transportation fuel. The feedstock for fuel ethanol in North America is primarily corn. Corn contains starch which is hydrolysed to glucose and then fermented to ethanol. In other countries, such as Brazil, fuel ethanol is made by fermenting the sugar in sugar cane. It is advantageous to have an additional source of sugars like glucose to make additional Biofuels.

At the other end of the spectrum of difficulty is cellulose. Cellulose is one of the most abundant organic materials on earth. It is present in many forms of biomass, including agricultural residues like corn Stover and corncobs, woody residues and other plant materials. Cellulose is a polymer of glucose, as is starch.

This invention is specifically targeting the highest lignin content materials to produce pure reactive cellulose of value on its own or as a feedstock that is easily hydrolysed to glucose and subsequently fermented to valuable product such as biofuels. Purified cellulose components are valuable for many purposes. Specifically, when purified, it may be more easily hydrolysed to glucose, which in turn may be more easily fermented to ethanol than in previous processes.

Lignocellulosic biomass is composed of three primary polymers that make up plant cell walls: Cellulose, hemicellulose, and lignin. Cellulose fibers are locked into a rigid structure of hemicellulose and lignin. Lignin and hemicelluloses form chemically linked complexes that bind water soluble hemicelluloses into a three dimensional array, cemented together by lignin. Lignin covers the cellulose microfibrils and protects them from enzymatic and chemical degradation. These polymers provide plant cell walls with strength and resistance to degradation, which makes lignocellulosic biomass a challenge to use as substrate for biofuel production.

Among the potential lignocellulosic feedstocks there is a range of lignin contents. Corncobs have a low lignin content (6%-8%), while woody crops have a medium lignin content of 10%-15%. Wood residues have even higher lignin content (20% to 30%)

Cellulose or β-1-4-glucan is a linear polysaccharide polymer of glucose made of cellobiose units. The cellulose chains are packed by hydrogen bonds in microfibrils. These fibrils are attached to each other by hemicelluloses, amorphous polymers of different sugars and covered by lignin. Hemicellulose is a physical barrier which surrounds the cellulose fibers and protects cellulose against degradation. Lignin is a very complex molecule constructed of phenylpropane units linked in a three dimensional structure which is particularly difficult to biodegrade. Lignin is the most recalcitrant component of the plant cell wall. There are chemical bonds between lignin, hemicellulose and cellulose polymers. Thus, it is desirable to use a lignocellulosic feedstock which is low in hemicellulose and lignin. There is evidence that the higher the proportion of lignin, the higher the resistance to chemical and biological hydrolysis. Pretreatment methods for the production of fermentable sugars from Miscanthus showed the existence of an inverse relationship between lignin content and the efficiency of enzymatic hydrolysis of sugars based polymers. Lignocellulosic microfibrils are associated in the form of macrofibrils. This complicated structure and the presence of lignin provide plant cell walls with strength and resistance to degradation, which also makes these materials a challenge to use as substrates for biofuel and bioproduct production. Thus, proper preparation and pretreatment is necessary to produce cellulose that is relatively pure and reacts well with catalyst such as enzymes.

The best method and conditions of pretreatment will vary and depend greatly on the type of lignocellulosic material used. Cellulose-lignin ratio is the main factor. Other parameters to consider are cellulose accessible surface area, degree of polymerization, crystallinity and degree of acetylation of hemicelluloses. An effective pretreatment should meet the following requirements: (a) production of pure reactive cellulosic fiber e.g. susceptible to enzymatic hydrolysis, (b) avoiding destruction of cellulose and hemicelluloses, and (c) avoiding formation of possible inhibitors for hydrolytic enzymes and fermenting microorganisms.

Several methods have been investigated for pretreatment of lignocellulosic materials to produce reactive cellulose. These methods are classified into physical pretreatments, biological pretreatments and physicochemical pretreatments. Physical and biological methods alone are not sufficient. Pretreatments that combine both chemical and physical processes are referred to as physicochemical processes. These methods are among the most effective and include the most promising processes for industrial applications. Lignin removal and hemicellulose hydrolysis are often nearly complete. Increase in cellulose surface area, decrease in cellulose degrees of polymerization and crystallinity greatly increase overall cellulose reactivity. Treatment rates are usually rapid. The steam explosion process is well documented. Batch and continuous processes were tested at laboratory and pilot scale by several research groups and companies. In steam explosion pretreatment, high pressure and hence high temperatures are used i.e. 160° C. to 260° C. for 1 min to 20 min. The pressure is suddenly reduced, which explosive decompression leads to an explosive decomposition of the materials, leading to defibrization of the lignocellulosic fibers.

Steam explosion pretreatment was successfully applied on a wide range of lignocellulosic biomasses with or without chemical addition. Acetic acid, dilute sulfuric acid, or sulfur dioxide are the most commonly used chemicals. In the autohydrolysis process, no acid is added as the biomass has a hemicellulose that is high in acetyl groups that are released to form acetic acid during the steaming process. The degree of acetylation of hemicelluloses varies among different sources of biomass. The pretreatment is not very effective in dissolving lignin, but it does disrupt the lignin structure and increases the cellulose's susceptibility to enzymatic hydrolysis.

The use of liquid ammonia instead of dilute acid effectively reduces the lignin fraction of the lignocellulosic materials. However, during ammonia fiber explosion pretreatment (AFEX) a part of the phenolic fragments of lignin and other cell wall extractives remain on the cellulosic surface. AFEX pretreatment does not significantly solubilize hemicellulose if compared to dilute-acid pretreatment. Consequently, hemicellulose and cellulose fractions remain intact and cannot be separated in solid and liquid streams. Furthermore, ammonia must be recycled after the pretreatment in order to reduce cost and protect the environment.

In the Organosolv process, lignocellulose is mixed with a mixture of organic solvents and water and heated to dissolve the lignin and part of the hemicellulose, leaving reactive cellulose in the solid phase. A variety of organic solvents such as alcohols, esters, ketones, glycols, organic acids, phenols, and ethers have been used. For economic reasons, the use of low-molecular-weight alcohols such as ethanol and methanol has been favored. A drawback of the Organolsolv process is the presence of hemicellulose with the lignin. An extensive overview of prior art organosolv processes is given in "Organosolv pulping"—A review and distillation study related to peroxyacid pulping".

In the process patented by Paszner and Chang, lignocellulosic biomass is saccharified to convert pentosans and hexosans to sugars by cooking under pressure at from 180° C. to 220° C. with acetone water solvent mixture carrying from 0.05 to 0.25% by weight of acid. Whole woody material is nearly dissolved by the process yielding mixed pentoses and hexoses. Hence, delignified pulp is hydrolyzed to glucose monomers that have to be recovered from the liquor.

The Alcell pulping process and further process developments have been applied with success on woody biomass. The problem with these processes is that they result in combined hemicellulose and lignin streams i.e. black liquor that is hard to separate afterwards. Lignin is precipitated from a black liquor produced by pulping wood at high temperatures and pressures with an aqueous lower aliphatic alcohol solvent i.e. lignin is precipitated by diluting the black liquor with water and an acid to form a solution with a pH of less than 3 and an alcohol content of less than 30%.

Pretreatment of lignocellulosic biomass is projected to be the single, most expensive processing step, representing about 20% of the total cost (65). In addition, the pretreatment type and conditions will have an impact on all other major operations in the overall conversion process from choice of feedstock through to size reduction, hydrolysis, and fermentation as well as on to product recovery, residue processing, and co-product potential. A number of different pretreatments involving biological, chemical, physical, and thermal approaches have been investigated over the years, but only those that employ chemicals currently offer the high yields and low costs vital to economic success. Among the most promising are pretreatments using a combination of dilute acid- or sulfur dioxide-catalyzed steam explosion and low molecular weight alcohols.

SUMMARY OF THE INVENTION

In order to address at least some disadvantages of the known art, the inventors have now developed a novel continuous two stage process. In the first stage steam heating takes place with added acid if required followed by pressing, with or without the presence of an eluent, to afford a hemicellulose fraction. In the second stage, acidic solvent extraction, washing and pressing provide a lignin rich stream and relatively pure reactive cellulose.

In the process of the invention, lignocelluosic biomass is presteamed and removed of air typically with a compression device then pretreated with high pressure steam, optionally with the addition of acid catalysts. By carefully choosing the temperature, time and catalyst content, a sufficient hydrolysis of hemicellulose is achieved, some high lignin biomass such as poplar for example does not require any or very little acid catalyst as it has sufficient acetyl residues in the hemicellulose. In the subsequent washing step, the pretreated biomass is pressed with or without addition of an eluent (e.g. water) under pressure to separate the hydrolysed hemicellulose. This extraction step also removes other water soluble or water suspended degradation products that in addition to the hydrolysed hemicelluloses which inhibit typical downstream processes such as enzymatic hydrolysis and fermentation. The hemicellulose is recovered and concentrated for value added use. It has been discovered that the full removal of the hemicellulose degradation and hydrolysis components is unnecessary for cost effective hydrolysis and fermentation and in fact complete removal is counterproductive for commercial process, they have found a practical range of 4% to 10% xylose as monomers and polymers in the final cellulose stream sufficient.

Following hemicellulose extraction, the biomass is then contacted with a solvent, and optionally an acid catalyst, cooked at an appropriate temperature and time to dissolve about 80% or more of the lignin. The biomass is then washed with a further application of solvent (e.g. ethanol), pressed and then rapidly depressurized to a recovery system. Solvent is recycled. Purified cellulose is washed with eluent to recover solvent. This cellulose fraction is now a valuable product, a) as high value pure reactive cellulose and b) a cellulose which is highly reactive to enzymatic hydrolysis.

The inventors of the present application have now surprisingly discovered that complete removal of lignin is neither required nor desirable for the achievement of the most economically viable pretreatment process for the purpose of hydrolyzing the cellulose with enzymes. The inventors have discovered a narrow range of extraction and lignin removal conditions at which lignin and lignin degradation products are still present, but reduced to a level where they have a much reduced inhibitory effect on the enzymes. The lignin content after extraction is preferably 5% to 8%. The extraction is achieved with the use of a lower volume of eluent and level of dilution and at equipment cost which requires sufficiently lower additional extraction and compound removal cost to render the process much more cost effective, practical and commercially viable. In effect, the additional extraction cost is thereby significantly less than the value of the increased ethanol yield achieved.

The reactive cellulose can be very effectively hydrolysed to glucose with an enzyme catalyst. This glucose can then be fermented to various high value products such as biofuel. A typical biofuel produced through yeast fermentation would be ethanol.

BRIEF DESCRIPTION OF THE DRAWING

FIG. 1 is a schematic illustration of a process in accordance with the invention.

DETAILED DESCRIPTION OF THE INVENTION

The process in accordance with the invention is a continuous two stage process. In the first stage, heat treatment is carried out under acid-catalyzed conditions and followed by pressing, with or without the presence of an eluent, to provide a hemicellulose fraction. In the second stage, acidic solvent extraction, washing and pressing provide a lignin rich stream and relatively pure reactive cellulose. Acid catalyzed hydrolysis of the hemicellulose can occur via autohydrolysis or with added acid catalyst or any combination therof depending on the feedstock.

A preferred process of the invention includes the steps of feed preparation, preheating, heating and catalyst addition, pretreatment, washing, solvent addition, solvent extraction, lignin removal, biomass recovery and ethanol recovery from purified cellulose.

The following description is one embodiment the invention is capable of other embodiments Step 1 Feed Preparation Biomass 10 is received, stored, cleaned and comminuted. Biomass moisture may be adjusted to desired range of 30-60% at this stage.

Step 2 Preheating

Prepared biomass is preheated or presteamed with live steam 20 at atmospheric pressure, in a preheating and conditioning or holding bin 30 to a temperature of up to 100° C., and preferably 85° C. to 95° C. for 10 to 60 minutes. The preheating is carried out to remove air and adjust a moisture content of the lignocellulosic biomass to between 30% and 60%. Steam and/or hot water are added. Air is vented from the bin 30 through an air vent 35.

Step 3 Heating and Catalyst Addition

Heated biomass is compressed in a modular screw device 40 to remove air through an air vent 50. Fatty acids, resins, esters or other compounds may exit the MSD device at this point (not shown on the diagram). The biomass is then fed into a pressurized upflow tube 70. The upflow tube 70 is sized to provide a 2 to 15 minutes holdup time. The dry matter content of the biomass varies from 30% to 50% prior to the addition of steam and catalyst if required.

The biomass is further heated in the up flow tube 70 to a pretreatment temperature of 150° C. to 200° C. by direct steam injection 60 or by indirect steam 61 in a jacketed section of the up flow tube.

If required, mineral acids or acid gases 65 are blended with the biomass, in an amount of 0 to 5% of the dry mass of the biomass, to catalyze the removal of hemicellulose and to activate the cellulose. The addition of acid 65 is made through a set of one or more nozzles along the length of the up flow tube.

The treated biomass moves through the up flow tube with the aid of a screw conveyor/mixer and is discharged into the pretreatment reactor 80.

Step 4 Pretreatment

The preheated and acidified biomass is discharged from the upflow tube 70 into the pretreatment reactor 80. The pretreatment reactor is sized to allow a residence time of up to two hours.

The pretreated biomass is continuously discharged from the pretreatment reactor to a second pressurized modular screw device 100.

Step 5 Washing Stage

Pressurized biomass, still at the pressure of the pretreatment reactor is mixed with wash water 90 as it exits the pretreatment reactor 80. The water 90 is pressed from the biomass as it passes through the modular screw device 100, still under pressure. The term modular screw device or/counter-current washer device is intended to describe in general a machine that uses pressing or other means to separate solids from liquid or air from solids. However, it is contemplated that the separation of solid from liquid and/or air from solid can be accomplished with various different types of machines which are suitable to carry out this function. Further water 90 may also be added along the pressing device 100 to achieve a greater extraction of Hemicellulose 110. The temperature of the wash water may vary from ambient temperature to 100° C. or higher to meet pressure requirements. In this washing stage a large fraction of the hemicellulose 110 is removed. The hemicellulose removal efficiency may vary from 50% to 90% or greater. In a preferred embodiment the hemicellulose is removed such that the remaining xylan and xylose measured as xylose in the de-lignified cellulose is between 4% to 10% most preferably 6%+/−1%.

Step 6 Solvent Addition

The dry matter content of the biomass is about 30% to 60% prior to solvent addition and steam injection.

After washing and pressing, pretreated pressurized biomass at a temperature of 30° C. to 100° C. or higher is fed from the modular screw device 100 into a second upflow tube 140 equipped with a screw conveyor/mixer. In the second upflow tube 140, the biomass is reheated with a combination of indirect steam 116 or direct steam 115 to a temperature of 180° C. to 200° C. The residence time in the second upflow tube 140 may vary from 5 to 15 minutes. The pressure of the second upflow tube 140 depends on the type of solvent used and the composition of the solvent. A solvent 130 such as ethanol is injected into the second upflow tube 140 under pressure through or more nozzles and blended with the biomass as it passes through the second upflow tube 140. A solvent 130 such as 40% to 60% ethanol in water is injected in the second upflow tube 140. The ratio of solvent to dry matter biomass is 2:1 to 10:1. Mineral acids 120 or other suitable acid catalysts may also be added to the second upflow tube 140 to assist in the hydrolysis and dissolution of lignin from the biomass. The pretreated biomass is blended with the solvent 130 and catalyst and is discharged from the second upflow tube 140 into a solvent extraction reactor 150.

Step 7 Solvent Extraction

The solvent extraction reactor 150 is designed to have a retention time of 15 minutes to 2 hours.

During the solvent extraction stage, about 80% to 90% of the lignin is dissolved and enters the solvent phase.

At the outlet of the extraction reactor, an amount of solvent is added to help wash the biomass from the reactor and to prepare the biomass for lignin separation in Step 7. The solvent and biomass is discharged from the reactor under pressure to a modular screw/counter current washer 160.

Step 8 Lignin Removal

The diluted biomass is pressed and extracted with solvent wash 170 in the modular screw/counter current washer 160 or something similar to achieve the same. About 95% to 99% of the solubilised lignin is removed from the biomass, along with some residual hemicellulose, extractives and other components. The wash stream is sent to the solvent recovery process 180. Preferably, evaporating/recovering just enough ethanol to avoid lignin precipitation, followed by a rapid decompression/drop in temperature through a spray dryer, leads to lignin precipitation and recovery (solid phase) and recovery of the remaining ethanol (flashed off/vapor phase). Preferably, the resulting washed biomass has a cellulose content of 75% to 95%, and more preferably about 80%.

Step 9 Biomass Recovery

The pressurized, washed biomass is flashed into a cyclone 190. Solvent vapors 200 are recovered from the cyclone. Purified cellulose 240 with low levels of residual solvent and lignin can be sent to the hydrolysis and fermentation stages.

Step 10 Ethanol Recovery from Purified Cellulose

The purified cellulose at atmospheric pressure is washed in a modular screw/counter current washer 210 with wash water 220 to remove and recover the solvent 230 remaining in the solid phase to provide a pure solvent free cellulose product. Preferably, the cellulose product has only 5% to 8% lignin remaining.

REFERENCES (1) Shapouri H et al. (1995) USDA Report 721. Estimating the net energy balance of corn ethanol.
(2) Shapouri H et al. (2002) USDA Report 813. The Energy Balance of corn ethanol: an update. (3) Chow J et al. (2003) Science, 302, 1528-1531 Energy resources and global development.
(3) Wald M L, Barrionuevo A (2007) New York Times, April 7th, The Energy challenge: A Renewed push for ethanol, without the corn.
(4) Greeg D (2008) Biocycle, 49, 11-47. Commercializing cellulosic ethanol.
(5) Hill J et al. (2006) Proc. Natl. Acad. Sci. USA, 103, 11206-11210. Environmental, economic, and energetic costs and benefits of biodiesel and ethanol biofuels.
(6) Farrell A E et al. (2006) Science, 311, 506-508. Ethanol can contribute to energy and environmental goals.
(7) Somerville C (2007) Current biology, 17, 115-119. Biofuels.
(8) Schuetzle D et al. (2007) Western Governors' Association. Alcohol fuels from biomass-Assessment of production technologies.
(9) Chum L, Overend R (2002) Fuel Processing technology, 71, 187-195. Biomass and renewable fuels.
(10) Wyman C E (1996) Taylor & Francis: Washington D.C., USA, Handbook on bioethanol: production and utilization.
(11) Delmer D P, Amor Y (1995) Plant Cell, 7, 987-1000. Cellulose biosynthesis.
(12) Morohoshi N (1991) In Wood and cellulosic chemistry; Hon, D. N. S, Shiraishi, N., Eds.; Marcel Dekker, Inc.: New York, USA, Chemical characterization of wood and its components. (14) Ha M A et al. (1998) Plant J. 1998, 16, 183-190. Fine structure in cellulose microfibrils: NMR evidence from onion and quince.
(15) Palmqvist E, Hahn-Hägerdal B (2000) Bioresource Technol., 74, 25-33. Fermentation of lignocellulosic hydrolysates. II: Inhibitors and mechanisms of inhibition.
(16) De Vrije T et al (2002) International journal of hydrogen energy, 27, 1381-1390. Pretreatment of miscanthus for hydrolgen production by thermotoga elfii.
(17) Galbe M, Zacchi G (2002) Appl Microbiol Biotechnol 59 618-628. A review of the production of ethanol from softwood.
(18) Torget R et al. (1991) Bioresource Technol., 35, 239-246. Dilute sulfuric acid pretreatment of hardwood bark.
(19) Donghai S et al. (2006) Chinese J. Chem. Eng., 14, 796-801. Effects of different pretreatment modes on the enzymatic digestibility of corn leaf and corn stalk.
(20) Sun Y, Cheng J (2002) Bioresources Technol., 83, 1-11. Hydrolysis of lignocellulosic materials for ethanol production: A review.
(21) McMillan J D (1994) In Enzymatic Conversion of Biomass for Fuels Production; Himmel, M. E., Baker, J. O., Overend, R. P., Eds.; ACS: Washington D.C., USA, 1994; pp. 292-324. Pretreatment of lignocellulosic biomass.
(22) Fan L et al (1982) Adv. Biochem. Eng. Biotechnol., 23, 158-183. The nature of lignocellulosics and their pretreatments for enzymatic hydrolysis.
(23) Mosier N et al. (2005) Bioresources Technol, 96, 673-686. Features of promising technologies for pretreatment of lignocellulosic biomass.
(24) Henley R G et al. (1980) Enzyme Microb. Tech., 2, 206-208. Enzymatic saccharification of cellulose in membrane reactors.
(25) Berlin A et al. (2006) J. Biotechnol., 125, 198-209. Inhibition of cellulase, xylanase and beta-glucosidase activities by softwood lignin preparations.
(26) Chandra R et al. (2007) Adv. Biochem. Eng. Biotechnol, 108, 67-93. Substrate pretreatment: The key to effective enzymatic hydrolysis of lignocellulosics?
(27) Kassim E A, El-Shahed A S (1986) Agr. Wastes, 17, 229-233. Enzymatic and chemical hydrolysis of certain cellulosic materials.
(28) Xu Z et al (2007) Biomass Bioenerg. 2007, 31, 162-167. Enzymatic hydrolysis of pretreated soybean straw.
(29) Vaccarino C et al (1987) Biol. Waste, 20, 79-88. Effect of $SO_2NaOH$ and $Na_2CO_3$ pretreatments on the degradability and cellulase digestibility of grape marc.
(30) Silverstein R A et al (2007) Bioresource Technol., 2007, 98, 3000-3011. A comparison of chemical pretreatment methods for improving saccharification of cotton stalks.
(31) Zhao X et al (2007) Bioresource Technol., 99, 3729-3736. Comparative study on chemical pretreatment methods for improving enzymatic digestibility of crofton weed stem.
(32) Gaspar M et al (2007) Process Biochem., 2007, 42, 1135-1139. Corn fiber as a raw material for hemicellulose and ethanol production.
(33) Saha B C, Cotta M A (2006) Biotechnol. Progr., 22, 449-453. Ethanol production from alkaline peroxide pretreated enzymatically saccharified wheat straw.
(34) Saha B C, Cotta M A (2007) Enzyme Microb. Tech., 41, 528-532. Enzymatic saccharification and fermentation of alkaline peroxide pretreated rice hulls to ethanol.
(35) Mishima D et al (2006) Bioresource Technol. 2006, 97, 2166-2172. Comparative study on chemical pretreatments to accelerate enzymatic hydrolysis of aquatic macrophyte biomass used in water purification processes.
(36) Sun X F et al (2005) Carbohyd. Res., 340, 97-106. Characteristics of degraded cellulose obtained from steam-exploded wheat straw.
(37) Chum H L (1985) Solar Energy Research Institute: Golden, Colo., 1-64. Evaluation of pretreatments of biomass for enzymatic hydrolysis of cellulose.
(38) Taherzedah M J, Karimi K (2007) Bioressources, 2, 472-499. Process for ethanol from lignocellulosic materials I: Acid-based hydrolysis processes.
(39) Ruiz E et al (2008) Enzyme Microb. Tech., 42, 160-166. Evaluation of steam explosion pretreatment for enzymatic hydrolysis of sunflower stalks.
(40) Ballesteros M et al. (2004) Process Biochem., 39, 1843-1848. Ethanol from lignocellulosic materials by a simultaneous saccharification and fermentation process (SFS) with *Kluyveromyces marxianus* CECT 10875.
(41) Negro M J et al (2003) Appl. Biochem. Biotechnol., 105, 87-100. Hydrothermal pretreatment conditions to enhance ethanol production from poplar biomass.
(42) Kurabi A et al (2005) Appl. Biochem. Biotechnol., 121-124. Enzymatic hydrolysis of steam exploded and ethanol organosolv-pretreated Douglas-firby novel and commercial fungal cellulases.
(43) Varga E et al (2004) Appl. Biochem. Biotechnol., 509-523. Optimization of steam pretreatment of corn stover to enhance enzymatic digestibility.

(44) Eklund R (1995) Bioresource Technol., 52, 225-229. The influence of SO2 and H2SO4 impregnation of willow prior to steam pretreatment.
(45) Yang B, Wyman C E (2004) Biotechnol. Bioeng, 86, 88-95. Effect of xylan and lignin removal by batch and flowthrough pretreatment on the enzymatic digestibility of corn stover cellulose.
(46) Alizadeh H et al (2005) Appl. Biochem. Biotechnol., 124, 1133-41. Pretreatment of switchgrass by ammonia fiber explosion (AFEX).
(47) Chundawat S P et al (2007) Biotechnol. Bioeng., 96, 219-231. Effect of particle size based separation of milled corn stover on AFEX pretreatment and enzymatic digestibility.
(48) Eggeman T, Elander R T. (2005) Bioresource Technol., 96, 2019-2025. Process and economic analysis of pretreatment technologies.
(49) Taherzadeh M J, Karimi K (2007) BioResources, 2, 707-738. Enzymatic-based hydrolysis processes for ethanol from lignocellulosic materials: A review.
(50) Neely W C (1984) Biotechnol. Bioeng., 26, 59-65. Factors affecting the pretreatment of biomass with gaseous ozone.
(51) Vidal P F, Molinier J (1988) Biomass, 16, 1-17. Ozonolysis of Lignin—Improvement of in vitro digestibility of poplar sawdust.
(52) Azzam A M (1989) J. Environ. Sci. Heal., 24, 421-433. Pretreatment of cane bagasse with alkaline hydrogen peroxide for enzymatic hydrolysis of cellulose and ethanol fermentation.
(53) Katzen R et al (1995) In The Alcohols Textbook; Lyons, T. P., Murtagh, J. E., Kelsall, D. R., Eds.; Nothingham University Press, 37-46. Use of cellulosic feedstocks for alcohol production.
(54) Araque E et al (2007) Enzyme Microb. Tech., 43, 214-219. Evaluation of organosolv pretreatment for the conversion of *Pinus radiata* D. Don to ethanol.
(55) Itoh H et al (2003) J. Biotechnol., 103, 273-280. Bioorganosolve pretreatments for simultaneous saccharification and fermentation of beech wood by ethanolysis and white rot fungi.
(56) Pan X et al (2006) Biotechnol. Bioeng., 94, 851-861. Bioconversion of hybrid poplar to ethanol and co-products using an organosolv fractionation process: optimization of process yields.
(57) Arato C et al (2005) Appl. Biochem. Biotechnol. 2005, 123, 871-882. The lignol approach to biorefining of woody biomass to produce ethanol and chemicals.
(58) Muurinen E (2000) University of Oulu, Finland, ISBN 951-42-5661-1. Organosolv pulping—A review and distillation study related to peroxyacid pulping. http://herkules.oulu.fi/isbn9514256611/isbn9514256611.pdf
(59) Pasner L, Chang P C (1983) U.S. Pat. No. 4,409,032
(60) Pasner L, Chang P C (1984) U.S. Pat. No. 4,470,851
(61) Lora J H et al (1988) U.S. Pat. No. 4,764,596, International publication WO 93/15261
(62) Van Heiningen A R P (1996) U.S. patent Ser. No. 08/621, 5096, International publication WO 97/36040
(63) Pye E K (2002) US patent #2002/0069987
(64) Petrus L (2007) US patent #2007/0034345 A1
(65) Yang B, Wyman C E (2007) Biofuels, Bioproducts and Biorefinering, 2, 26-40. Pretreatment: the key to unlocking low-cost cellulosic ethanol.

What is claimed is:

1. A process for producing reactive cellulose from lignocellulosic biomass having a hemicellulose content and a lignin content, comprising the steps of:
   (a) pretreating the lignocellulosic biomass under pressure with steam and solvent to obtain pressurized solvent washed biomass by
      (a1) maintaining the lignocellulosic biomass at a pressure equivalent to a saturated steam pressure at a first preselected temperature of 150° C. to 200° C. until a preselected degree of hemicellulose hydrolysis is achieved;
      (a2) pressing the pretreated biomass while under pressure to remove 80% to 90% of the hemicellulose hydrolyzate to obtain pretreated extracted biomass;
      (a3) contacting the pretreated extracted biomass while under pressure and at 180° C. to 200° C. with a solvent to hydrolyze and dissolve lignin in the pretreated extracted biomass;
      (a4) maintaining the pretreated extracted biomass in contact with the solvent for a selected period of time to obtain solvent treated biomass;
      (a5) pressing the solvent treated biomass using a modular screw device while under pressure for removing solvent and dissolved lignin; and
      (a6) washing the pressed solvent treated biomass under pressure by adding additional solvent to said modular screw device to remove additional lignin from the pretreated biomass mixture and further pressing the pretreated biomass mixture to obtain a pressurized solvent washed biomass;
   (b) generating a purified cellulose stream and a vapour stream by flashing the pressurized solvent washed biomass into a separator to subject the pressurized solvent washed biomass to explosive decompression and subsequent separation into the purified cellulose stream and the vapour stream; and
   (c) collecting the purified cellulose stream and recovering the solvent in the vapor stream.

2. The process of claim 1, wherein an acid catalyst is added to the lignocellulosic biomass during the step of maintaining the lignocellulosic biomass under pressure.

3. The process of claim 1, wherein an eluent is added to the pretreated biomass during the step of pressing the pretreated biomass.

4. The process of claim 1, wherein an acid catalyst is contacted with the pretreated extracted biomass and maintained for the selected period of time.

5. The process of claim 1, further comprising: (a7) adding a second stream of solvent to the pressed solvent treated biomass in said modular screw device, and pressing the solvent treated biomass under pressure for removing solvent and dissolved lignin to obtain a biomass with a cellulose content of 75% to 95%, and to recover the solvent.

6. The process of claim 5, wherein the cellulose content is about 80%.

7. The process of claim 1, wherein the separator is a cyclone separator and the stream of cellulose is washed with water to remove and collect additional solvent.

8. The process of claim 1, wherein the purified cellulose stream is washed with water for additional purification of the cellulose stream and additional solvent recovery.

9. The process of claim 1, wherein the solvent is selected from the group consisting of alcohol, ketones and triethylene glycol.

10. The process of claim 9, wherein the alcohol is methanol, ethanol, or butanol.

11. The process of claim 1, wherein the first preselected temperature is 160° C. to 180° C.

12. The process of claim 1, wherein an initial step of steam preheating is carried out prior to pretreating the lignocellulosic biomass, the preheating is carried out at a preselected temperature of up to 100° C. for a period of 10 to 60 minutes to remove air and adjust a moisture content of the lignocellulosic biomass to between 30% and 60%.

13. The process of claim 4, wherein the acid catalyst is up to 5% of the dry mass of the pretreated extracted biomass.

14. The process of claim 13, wherein the acid catalyst is sulfuric acid.

15. The process of claim 3, wherein the eluent is a solution including water.

16. The process of claim 1, wherein the solvent is added in a ratio of 2:1 up to 10:1 compared to a solid content of the pretreated extracted biomass.

17. The process of claim 16, wherein the ratio is 4:1 up to 7:1.

18. The process of claim 1, wherein the selected period of time is 20 minutes to 2 hours.

19. The process of claim 1, wherein the step of pressing the pretreated biomass is controlled such that the purified cellulose stream has between 4% to 10% xylose sugar content as monomer or polymers thereof.

20. The process of claim 1, wherein the step of pressing the pretreated biomass is controlled such that the purified cellulose stream has between 6%+/−1% xylose sugar content as monomer or polymers thereof.

21. The process of claim 1, wherein the step of solvent extraction and washing the pretreated biomass mixture is controlled to achieve a lignin content of 5% to 8% in the purified cellulose stream.

22. The process of claim 18, wherein the step of solvent extraction and washing the pretreated biomass mixture is controlled to achieve a lignin content of 5% to 8% in the purified cellulose stream.

23. The process of claim 2, wherein the acid catalyst is up to 5% of the dry mass of the lignocellulosic biomass.

* * * * *